(12) United States Patent
Morishima

(10) Patent No.: US 11,471,029 B2
(45) Date of Patent: Oct. 18, 2022

(54) VARIABLE STIFFNESS ACTUATOR, ENDOSCOPE, AND POWER SUPPLY METHOD

(71) Applicant: OLYMPUS CORPORATION, Tokyo (JP)

(72) Inventor: Tetsuya Morishima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 415 days.

(21) Appl. No.: 16/654,401

(22) Filed: Oct. 16, 2019

(65) Prior Publication Data

US 2020/0046204 A1 Feb. 13, 2020

Related U.S. Application Data

(63) Continuation of application No. PCT/JP2017/015694, filed on Apr. 19, 2017.

(51) Int. Cl.
*A61B 1/005* (2006.01)
*A61B 1/00* (2006.01)
*F03G 7/06* (2006.01)

(52) U.S. Cl.
CPC ........ *A61B 1/0058* (2013.01); *A61B 1/00078* (2013.01); *A61B 1/00114* (2013.01); *F03G 7/065* (2013.01)

(58) Field of Classification Search
CPC ............ A61B 1/00078; A61B 1/00114; A61B 1/0058; A61B 1/00025
See application file for complete search history.

(56) References Cited

U.S. PATENT DOCUMENTS

| 5,482,029 A | 1/1996 | Sekiguchi et al. |
| 2012/0029287 A1* | 2/2012 | Wieters ................. A61B 1/051 600/133 |
| 2018/0080437 A1* | 3/2018 | Morishima .......... A61B 1/0057 |

FOREIGN PATENT DOCUMENTS

| JP | S58-101601 U | 7/1983 |
| JP | H06-70879 A | 3/1994 |

(Continued)

OTHER PUBLICATIONS

English translation of International Preliminary Report on Patentability dated Oct. 31, 2019, together with the Written Opinion received in related International Application No. PCT/JP2017/015694.

(Continued)

*Primary Examiner* — Aaron B Fairchild
(74) *Attorney, Agent, or Firm* — Scully, Scott, Murphy & Presser, P.C.

(57) ABSTRACT

A variable stiffness actuator includes a shape-memory member, and a heater configured to receive power to heat the shape-memory member so as to cause the shape-memory member to change from a first phase as a low stiffness state to a second phase as a high stiffness state showing a higher stiffness than the low stiffness state. The actuator also includes a first conductive wire having one end connected to the heater and constituting a part of a power supply line for the heater, and a second conductive wire having one end connected to the other end of the first conductive wire, thicker than the first conductive wire, and having an electrical resistance per unit length lower than that of the first conductive wire.

11 Claims, 5 Drawing Sheets

(56) References Cited

FOREIGN PATENT DOCUMENTS

| WO | WO 2016/121060 A1 | 8/2016 |
| WO | WO 2016/185561 A1 | 11/2016 |

OTHER PUBLICATIONS

International Search Report dated Jun. 27, 2017 issued in PCT/JP2017/015694.
Chinese Office Action dated Apr. 13, 2021 received in 201780089681.5.

* cited by examiner

VARIABLE STIFFNESS ACTUATOR, ENDOSCOPE, AND POWER SUPPLY METHOD

CROSS-REFERENCE TO RELATED APPLICATIONS

This application is a Continuation Application of PCT Application No. PCT/JP2017/015694, filed Apr. 19, 2017, the entire contents of which are incorporated herein by reference.

BACKGROUND OF THE INVENTION

1. Field of the Invention

The present invention relates to a variable stiffness actuator configured to provide different degrees of bending stiffness to a flexible member.

2. Description of the Related Art

A variable stiffness actuator, installed in a flexible insertion apparatus such as an endoscope etc., and capable of changing bending stiffness (hardness) of a flexible member constituting a flexible tube section of such an apparatus, has been developed. For example, International Publication No. 2016/121060 describes a variable stiffness actuator configured to provide different degrees of bending stiffness (hardness) to a flexible member using phase transition of a shape-memory member. In the variable stiffness actuator, an inducing member causes the shape-memory member to undergo a phase transition by virtue of the power (current) supplied to the inducing member from a power supply section.

BRIEF SUMMARY OF THE INVENTION

A variable stiffness actuator includes a shape-memory member, and a heater configured to receive power to heat the shape-memory member so as to cause the shape-memory member to change from a first phase as a low stiffness state to a second phase as a high stiffness state showing a higher stiffness than the low stiffness state. The actuator also includes a first conductive wire having one end connected to the heater and constituting a part of a power supply line for the heater, and a second conductive wire having one end connected to the other end of the first conductive wire, thicker than the first conductive wire, and having an electrical resistance per unit length lower than that of the first conductive wire.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments will be described with reference to the drawings.

First Embodiment

Figure 1:
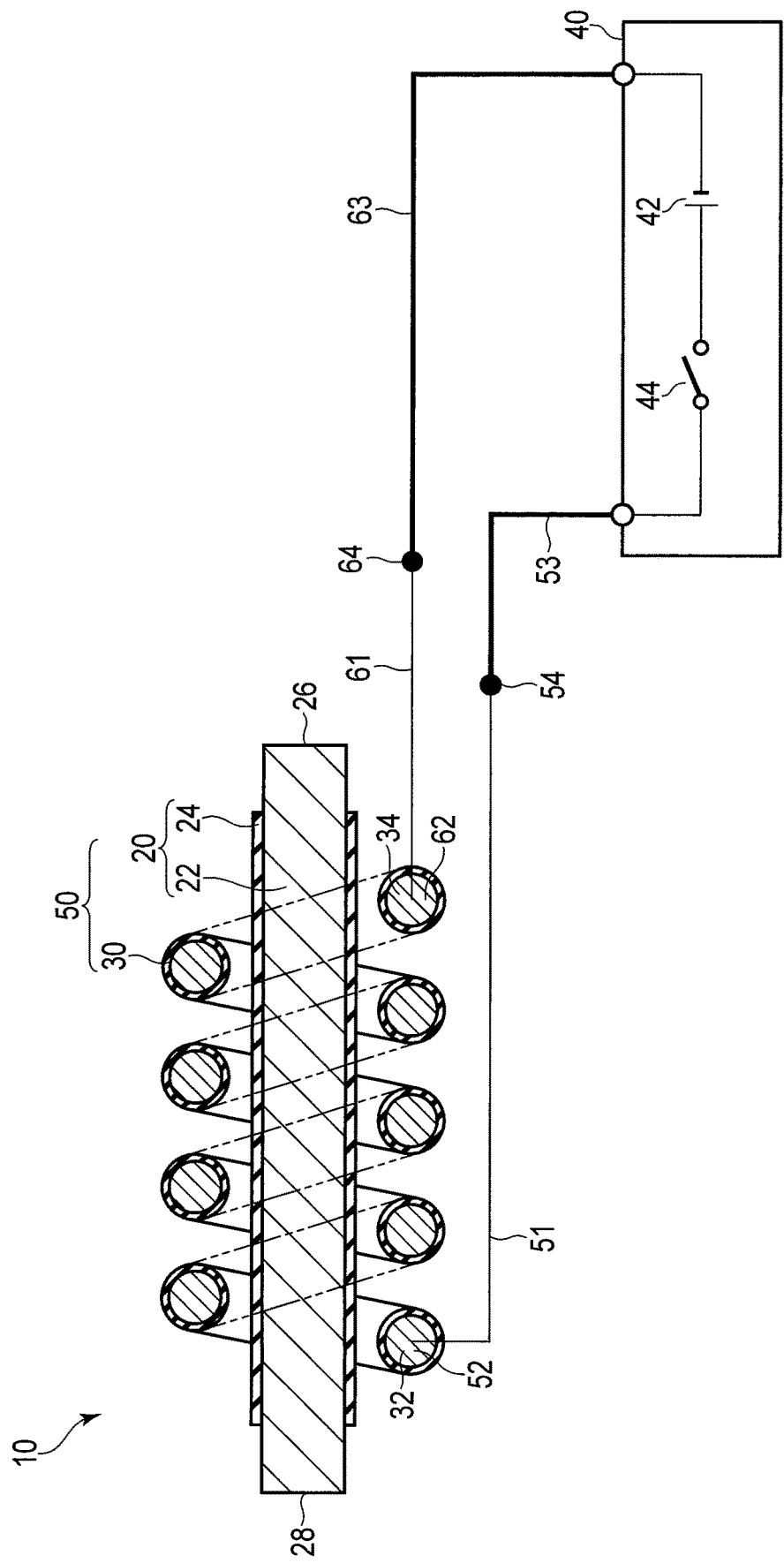
FIG. 1 is a figure showing a variable stiffness actuator according to a first embodiment.

FIG. 1 is a figure showing a variable stiffness actuator 10 according to a first embodiment of the present invention. The variable stiffness actuator 10 includes a shape-memory member 20, an inducing member 30, and a power supply section 40.

The shape-memory member 20 is capable of undergoing a change of phase (phase transition) between a first phase and a second phase, so as to take different bending stiffness states, in other words, different stiffness degrees. In the first phase, the shape-memory member 20 is in a soft state (low stiffness state), in which it is easily deformed by an external force, thereby indicating a low elastic coefficient. In the second phase, the shape-memory member 20 is in a hard state (high stiffness state), in which it tends to resist external force to restore a memorized shape, thereby indicating a high elastic coefficient. That is, when the shape-memory member 20 is in the second phase, it assumes the high stiffness state with high stiffness compared to the low stiffness state. The memorized shape may be either a bent shape or a linear shape. The external force means a force that can deform the shape-memory member 20. Gravity is also considered to be a part of the external force.

The shape-memory member 20 is mainly constituted from, for example, a shape memory alloy. The shape memory alloy may be, for example, an alloy including, but not limited to, NiTi (nickel titanium). Further, the shape-memory member 20 is not limited to the above and may be mainly constituted from other materials such as a shape memory polymer, shape memory gel, and shape memory ceramics.

The shape memory alloy, which mainly constitutes the shape-memory member 20, for example, undergoes a phase transition between a martensite phase and an austenite phase. Such a shape memory alloy plastically deforms relatively easily under external force during the martensite phase. That is, such a shape memory alloy indicates a low elastic coefficient during the martensite phase. On the other hand, such a shape memory alloy resists external force and does not easily deform during the austenite phase. Even if the alloy deforms due to a large external force, the hyperelasticity will be exhibited once the large external force disappears and the alloy will return to the memorized shape. Therefore, the shape memory alloy indicates a high elastic coefficient during the austenite phase.

The shape-memory member 20 includes an elongated main body 22 formed from conductive materials such as, for example, a shape memory alloy, and an insulating film 24 provided around the main body 22 in such a manner to encase it. The insulating film 24 works to prevent a short circuit between the shape-memory member 20 and the inducing member 30. The insulating film 24 is provided to cover at least a part facing the inducing member 30. FIG. 1 shows an aspect where an outer peripheral surface of the main body 22 is partially covered; however, this is not a limitation, and the entire outer peripheral surface of the main body 22 may be covered or the entire main body 22 may be covered.

Thus, the shape-memory member 20 is an elongated wire shaped-member extending in a longitudinal direction from a first end 26 to a second end 28.

The inducing member 30 is a member configured to cause the shape-memory member 20 to transit in phase (phase transition) between the first phase and the second phase. The inducing member 30 is constituted by, for example, a heater. That is, the inducing member 30 has a characteristic of generating heat in response to, for example, the supply of current flowing through the inducing member 30. The inducing member 30 may be any member configured to generate heat and is thus not limited to a heater, and may be constituted from an imaging element (for example, CCD), light guide, and other elements or members etc. The inducing member, which generates heat to transmit heat to the shape-memory member 20 causes the shape-memory member 20 to undergo a transition of phase from the first phase to the second phase.

The inducing member 30 is mainly constituted from a conductive material. The inducing member 30 includes, for example, a heating wire formed from a conductive material and an insulating film provided around the heating wire. The insulating film works to prevent the occurrence of a short circuit between the shape-memory member 20 and the inducing member 30, as well as the occurrence of a short circuit between the adjacent parts of the heating wire of the inducing member 30. If the insulating film of the inducing member 30 provides a secure short circuit prevention function, the insulating film 24 of the shape-memory member 20 may be omitted.

The inducing member 30 is arranged near the shape-memory member 20. In FIG. 1, the inducing member 30 is a coil shape (winding shape) extending in a longitudinal direction, and the elongated wire shape-memory member 20 is arranged within an inner space of the inducing member 30. By such an arrangement, the heat from the inducing member 30 is transmitted to the shape-memory member 20.

Figure 2:
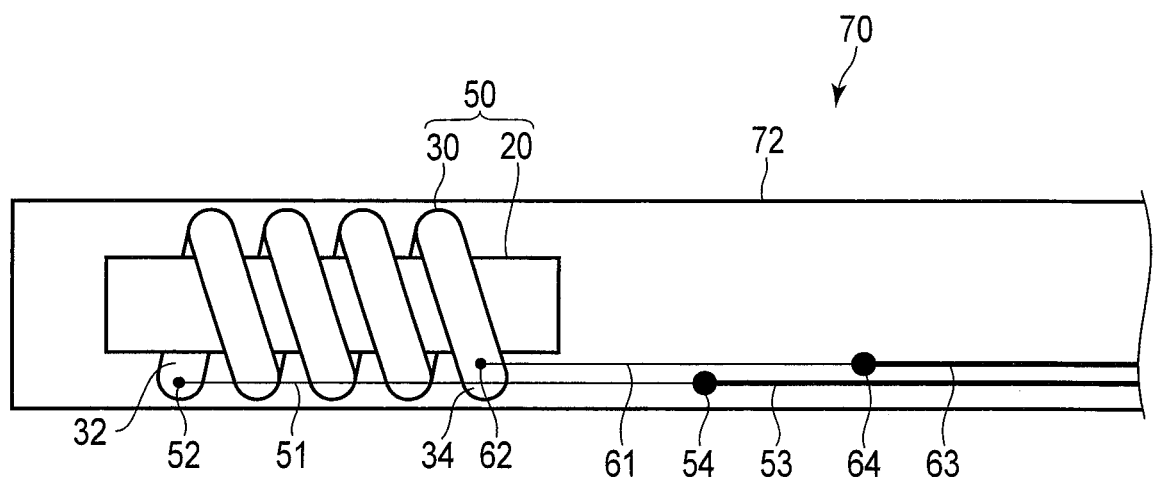
FIG. 2 is a figure outlining an insertion section of an endoscope provided with a variable stiffness actuator.

FIG. 2 is a figure outlining an insertion section (flexible member) 72 of an endoscope 70 provided with the variable stiffness actuator 10. The endoscope 70 is an example of a flexible tube insertion apparatus in which the variable stiffness actuator 10 is installed.

The shape-memory member 20 and the inducing member 30 constitute a variable stiffness section 50. The variable stiffness section 50 is arranged in a flexible member constituting a flexible elongated insertion section 72 of the endoscope 70. Thus, the variable stiffness actuator 10 is attached to the insertion section 72, which is the flexible member, and has a function to provide different stiffness degrees to the insertion section 72 by taking different bending stiffness states, that is, different degrees of hardness.

In an exemplary instance, when the shape-memory member 20 is in the aforementioned first phase, the variable stiffness actuator 10 provides a relatively low stiffness to the insertion section 72. That is, a part of the insertion section 72 where low bending stiffness is in effect courtesy of the variable stiffness section 50 can be easily bent under the influence of the external force. When the shape-memory member 20 is in the second phase, the variable stiffness actuator 10 provides a relatively high stiffness to the insertion section 72. Thus, a part of the insertion section 72 where high bending stiffness is in effect courtesy of the variable stiffness section 50 will not bend easily under the influence of the external force.

Further, in FIG. 2, the variable stiffness section 50 is positioned near the distal end of the insertion section 72 of the endoscope 70; however, the position of the variable stiffness section 50 is not limited. The variable stiffness section 50 may be arranged at any desired position where the stiffness change is desired in the insertion section 72. Moreover, the length of the variable stiffness section 50 can be set to any desired length.

The power supply section 40 includes a power supply 42 and a switch 44. The power supply section 40 supplies a current that flows through the inducing member 30 to the inducing member 30 in response to the switching "on" of the switch 44, that is, a close operation, and stops the supply of current to the inducing member 30 in response to the switching "off" of the switch 44, that is, an open operation. The inducing member 30 generates heat in accordance with the supply of the current. The power supply section 40 is controlled by a controller, which is not illustrated.

The following explains the configuration and arrangement of conductive wires electrically connecting the inducing member 30 and the power supply section 40 in the present embodiment. In the present embodiment, two types of conductive wires 51, 53, 61, and 63 with lower electrical resistance per unit length than the inducing member 30 (heating wire) are used to improve the responsiveness of the inducing member 30, and accordingly of the shape-memory member 20, to the power (current) supplied from the power supply section 40. The responsiveness means, for example, a response, i.e., reactivity, of the shape-memory member 20 during the shape-memory member 20 transits in phase between the first phase and the second phase according to the power supplied from the power supply section 40.

The first conductive wires 51 and 61 each are a conductive wire with low electrical resistance per unit length that uses a material with lower electrical resistance than the inducing member 30. Thus, the first conductive wires 51 and 61 do not generate heat even if the same current as in the inducing member 30 flows.

One end of the first conductive wire 51 is connected to a first end 32 of the inducing member 30 by a first joint 52. One end of the first conductive wire 61 is connected to a second end 34 of the inducing member 30, which is different from the first end 32, by a first joint 62. As shown in FIGS. 1 and 2, the first end 32 is an end that is farther from the power supply section 40 than the second end 34 in the longitudinal direction of the variable stiffness section 50. In other words, the second end 34 is an end that is closer to the power supply section 40 than the first end 32. As seen from the above, both ends 32 and 34 of the inducing member 30 are respectively connected to the first conductive wires 51 and 61 by the first joints 52 and 62. The first joint 52 is an electrical contact between the first conductive wire 51 and the inducing member 30, and the first joint 62 is an electrical contact between the first conductive wire 61 and the inducing member 30. Each connection by the first joints 52 and 62 is, for example, formed by soldering, brazing, welding, or conductive adhesive.

The second conductive wires 53 and 63 are thicker than the first conductive wires 51 and 61. Similar to the first conductive wires 51 and 61, the second conductive wires 53 and 63 each are a conductive wire with low electrical resistance per unit length that uses a material with lower electrical resistance than the inducing member 30. That is, the magnitude of the electrical resistance is inversely proportional to the thickness (cross sectional area) of the conductive wire; thus, the second conductive wires 53 and 63, which are thicker than the first conductive wires 51 and 61, have a lower electrical resistance per unit length than the first conductive wires 51 and 61. The second conductive wires 53 and 63 also do not generate heat even if the same current as in the inducing member 30 flows.

One end of the second conductive wire 53 is connected to the other end of the first conductive wire 51 by a second joint 54. One end of the second conductive wire 63 is connected to the other end of the first conductive wire 61 by a second joint 64. The other ends of the second conductive wires 53 and 63 are connected to the power supply section 40. The second joint 54 is an electrical contact between the first conductive wire 51 and the second conductive wire 53, and the second joint 64 is an electrical contact between the first conductive wire 61 and the second conductive wire 63. Each connection by the second joints 54 and 64 is, for example, also formed by soldering, brazing, welding, or conductive adhesive.

The second joints 54 and 64 are each arranged at a position closer to the power supply section 40 than the first end 26 of the shape-memory member 20 in the longitudinal direction. Further, of the two second joints 54 and 64, the second joint 64 is arranged at a position closer to the power supply section 40 than the other second joint 54. That is, the two second joints 54 and 64 are arranged so as not to overlap with each other in the longitudinal direction.

In the present embodiment, the second conductive wires 53 and 63 are each arranged at a position closer to the power supply section 40 than the first end 26, which is a terminal end of the shape-memory member 20, in the longitudinal direction. Thus, in the insertion section 72 as shown in FIG. 2, the second conductive wires 53 and 63 are arranged at a spacious location where the shape-memory member 20 does not extend. Therefore, since the second conductive wires 53 and 63, which are thicker than the first conductive wires 51 and 61, can be arranged in the insertion section 72, the electrical resistance per unit length can be decreased.

Generally, since the joint may cause the failure of the variable stiffness section 50, the joint is desirably arranged away from the variable stiffness section 50 in the longitudinal direction. In the present embodiment, the second joints 54 and 64 between the first conductive wires 51 and 61 and the second conductive wires 53 and 63 are each arranged at a position closer to the power supply section 40 than a position of the variable stiffness section 50 in the longitudinal direction. Thus, the positions of the variable stiffness section 50 and the second joints 54 and 64 do not overlap in the longitudinal direction. Therefore, joint-induced failures in the variable stiffness section 50 are less likely to happen.

When joints overlap in the longitudinal direction, the diameter of the overlapped portion must be thicker. Since the joints are hard, overlapping may also cause a failure. In the present embodiment, since the two second joints 54 and 64 are displaced from each other and do not overlap each other in the longitudinal direction, the embodiment is free from the diameter increase and the failure occurrence due to the overlapping portion.

In contrast to the first conductive wires 51 and 61 that may be relatively short, the second conductive wires 53 and 63 are assumed to have a length of several meters in order to transmit power between the power supply section 40 and a position near the variable stiffness section 50 in the variable stiffness actuator 10. Thus, decreasing the electrical resistance of the second conductive wires 53 and 63 as greatly as possible, in other words, increasing their electrical conductivity can prevent the voltage drop in the second conductive wires 53 and 63. Through the above configuration, the power can be efficiently supplied to the inducing member 30, so that the responsiveness of the inducing member 30, and accordingly of the shape-memory member 20, to the supplied power can be improved. According, the present embodiment can provide the variable stiffness actuator 10 with an improved responsiveness by a simple configuration.

Second Embodiment

Figure 3:
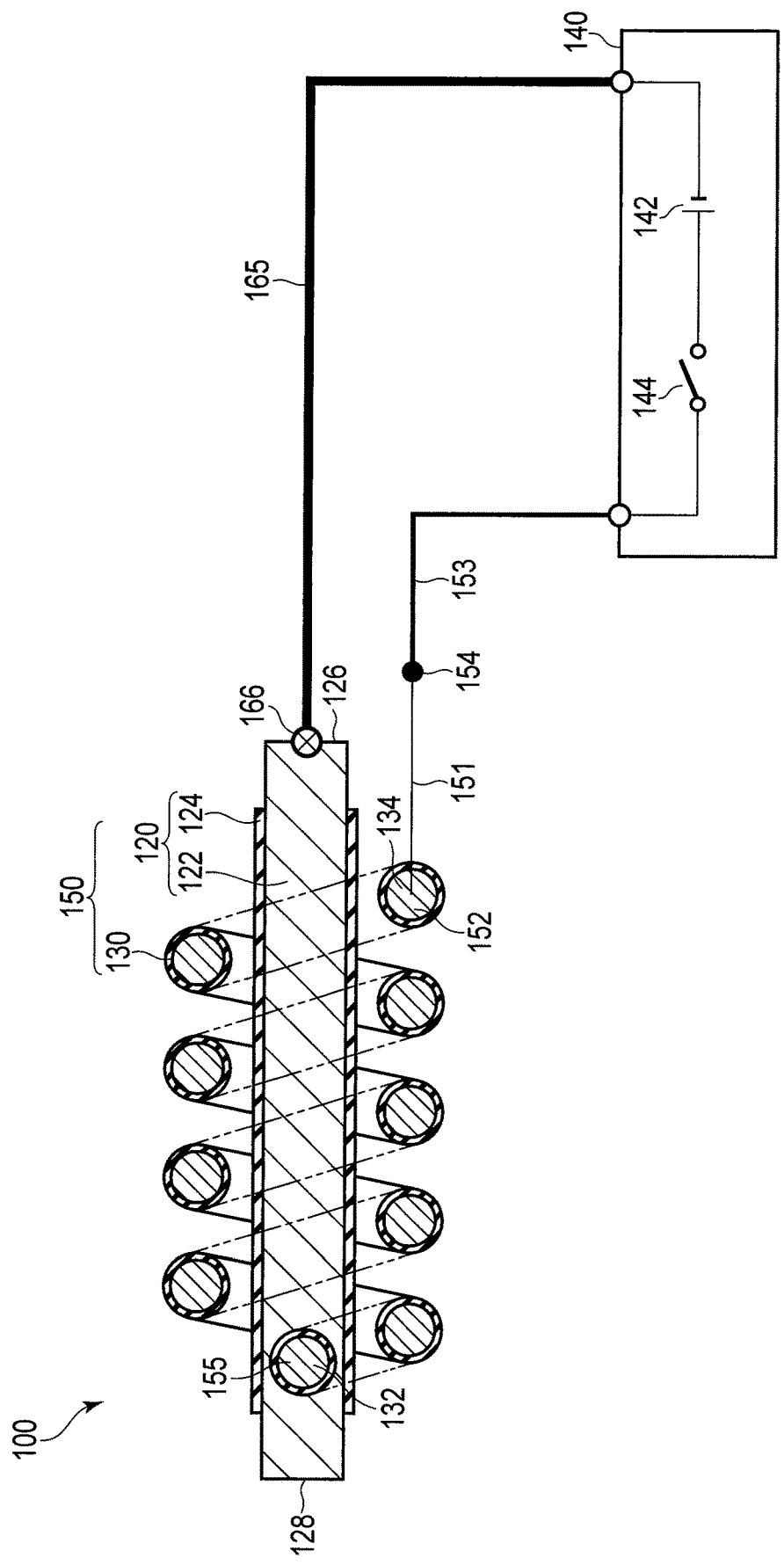
FIG. 3 is a figure showing a variable stiffness actuator according to a second embodiment.

FIG. 3 is a figure showing a variable stiffness actuator 100 according to a second embodiment of the present invention. The variable stiffness actuator 100 includes a shape-memory member 120, an inducing member 130, and a power supply section 140. The configurations and the arrangements of the shape-memory member 120 (main body 122 and insulating film 124), inducing member 130, and power supply section 140 (power supply 142 and switch 144) may all conform to those of the shape-memory member 20 (main body 22 and insulating film 24), inducing member 30 and power supply section 40 (power supply 42 and switch 44) of the first embodiment. Therefore, the following explains the matters of such configurations and arrangements that are different from the first embodiment, and explanation of the common matters will be omitted.

In the present embodiment, a first end 132 of the inducing member 130 is connected to the shape-memory member 120 by a third joint 155. The third joint 155 is arranged at a position close to a second end 128 of the shape-memory member 120 in the longitudinal direction.

The following explains the configuration and arrangement of conductive wires 151, 153, and 165 electrically connecting the shape-memory member 120, the inducing member 130, and the power supply section 140. In the present embodiment, the conductive wires 151, 153, and 165 that are three types of wires with lower electrical resistance per unit length than the inducing member 130 are used to improve the responsiveness of the inducing member 130 and the shape-memory member 120 to the power supplied from the power supply section 140.

Similar to the first conductive wire 51 of the first embodiment, the first conductive wire 151 is a conductive wire with low electrical resistance per unit length that uses a material with lower electrical resistance than the inducing member 130. One end of the first conductive wire 151 is connected to a second end 134 of the inducing member 130 by a first joint 152. The second end 134 is an end that is closer to the power supply section 140 than the first end 132 in the longitudinal direction of a variable stiffness section 150.

Similar to the second conductive wire 53 of the first embodiment, the second conductive wire 153 is thicker than the first conductive wire 151. The second conductive wire 153 is a conductive wire with low electrical resistance per unit length that uses a conductive wire with lower electrical resistance than the inducing member 130, which is similar to the first conductive wire 151. One end of the second conductive wire 153 is connected to the other end of the first conductive wire 151 by a second joint 154. The other end of the second conductive wire 153 is connected to the power supply section 140.

The third conductive wire 165 is desirably thicker than the second conductive wire 153, so as to have lower electrical resistance per unit length than the second conductive wire 153. However, if the third conductive wire 165 has the electrical resistance that is lower than that of the first conductive wire 151, the electrical resistance of the third conductive wire 165 may be similar to that of the second conductive wire 153. That is, if the electrical resistance of the second conductive wire 153 is sufficiently low, the electrical resistance of the second conductive wire 153 and that of the third conductive wire 165 may be similar.

One end of the third conductive wire 165 is connected to a first end 126 of the shape-memory member 120 by a fourth joint 166. Thus, the shape-memory member 120 constituted by the conductive material and the third conductive wire 165 are connected by the fourth joint 166, and the shape-memory member 120 serves as a conductive wire through which the current from the power supply section 240 flows. The other end of the third conductive wire 165 is connected to the power supply section 140.

The first joint 152 is an electrical contact between the first conductive wire 151 and the inducing member 130. The second joint 154 is an electrical contact between the first conductive wire 151 and the second conductive wire 153. The third joint 155 is an electrical contact between the shape-memory member 120 and the inducing member 130. The fourth joint 166 is an electrical contact between the third conductive wire 165 and the shape-memory member 120. Each connection by the joints 152, 154, 155, and 166 is, for example, also formed by soldering, brazing, welding, or conductive adhesive. In the present embodiment, the joints 152, 154, 155, and 166 are displaced from one another so that their positions do not overlap in the longitudinal direction.

The third conductive wire 165 is assumed to have a length of several meters in order to transmit power between the power supply section 140 and a position near the variable stiffness section 150 in the variable stiffness actuator 100. Thus, decreasing the electrical resistance of the third conductive wire 165 as greatly as possible can prevent the voltage drop in the third conductive wire 165. Through the above configuration, the power can be efficiently supplied to the inducing member 130, so that the responsiveness of the inducing member 130 and the shape-memory member 120 to the supplied power can be improved. According, similar to the first embodiment, the present embodiment can also provide the variable stiffness actuator 100 with improved responsiveness.

Furthermore, in the present embodiment, since the shape-memory member 120 constituted by the conductive material and the third conductive wire 165 are connected by the fourth joint 166, the first conductive wire 151 is the only conductive wire that overlaps with the variable stiffness section 150 in the longitudinal direction. In other words, wire-saving is possible by employing the shape-memory member 120 as a conductive wire through which the current from the power supply section 240 flows.

Third Embodiment

Figure 4:
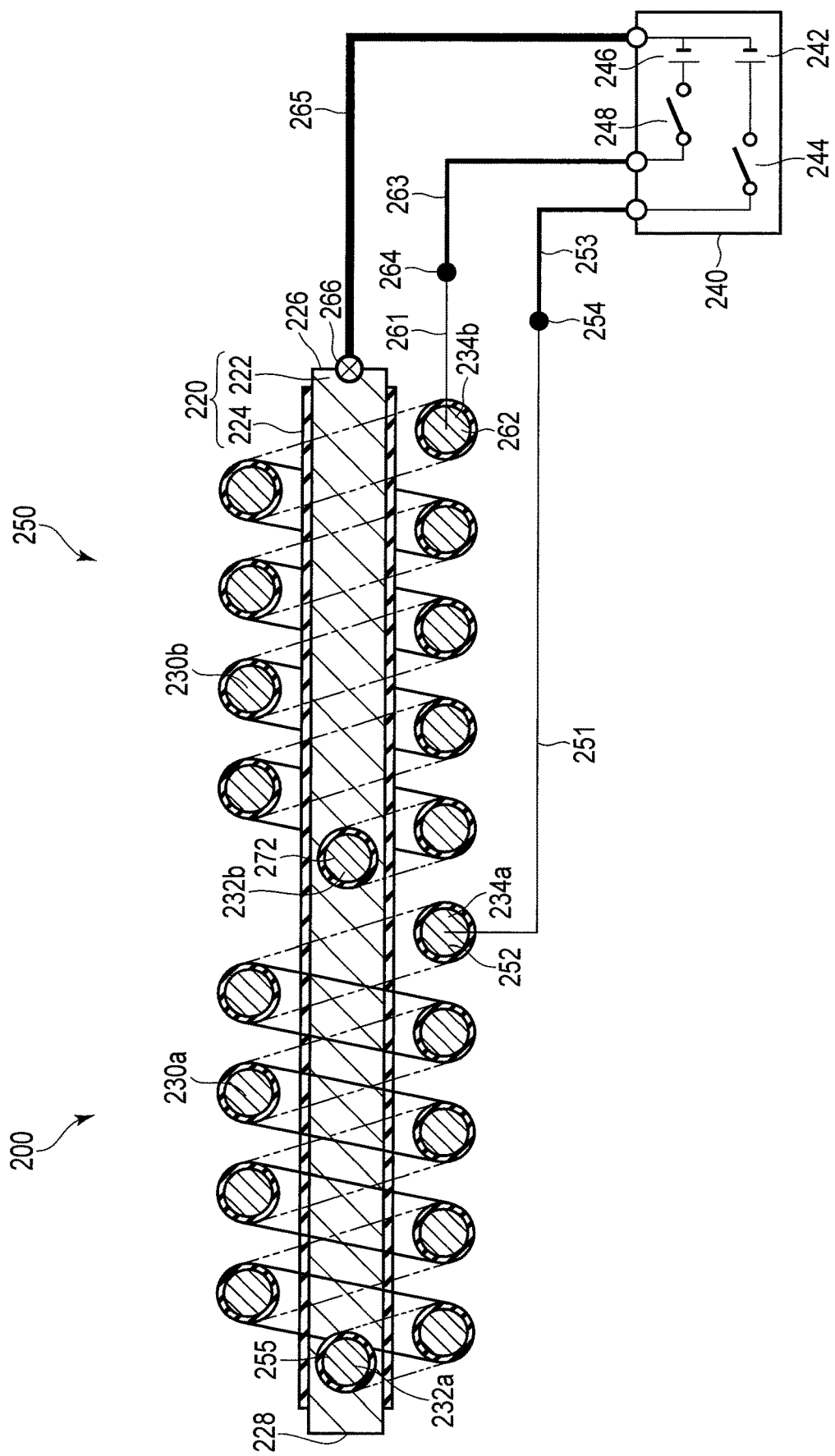
FIG. 4 is a figure showing a variable stiffness actuator according to a third embodiment.

FIG. 4 is a figure showing a variable stiffness actuator 200 according to a third embodiment of the present invention. The variable stiffness actuator 200 comprises a shape-memory member 220, two inducing members, that is, a first inducing member 230a and a second inducing member 230b, and a power supply section 240. The configurations of the shape-memory member 220 (main body 222 and insulating film 224), and each of the first inducing member 230a and second inducing member 230b may entirely conform to those of the shape-memory member 20 (main body 22 and insulating film 24) and inducing member 30 of the first embodiment. Therefore, the following explains the matters of such configurations that are different from the first embodiment, and explanation of the common matters will be omitted.

In the present embodiment, the first inducing member 230a and the second inducing member 230b are arranged near the shape-memory member 220. The configurations of the first inducing member 230a and the second inducing member 230b are the same as the inducing member 30 according to the first embodiment. The second inducing member 230b is arranged closer to the power supply section 240 than the first inducing member 230a in the longitudinal direction of a variable stiffness section 250.

The power supply section 240 includes a first power supply 242 and a first switch 244, and a second power supply 246 and a second switch 248. The power supply section 240 supplies a current flowing through respective one of the first inducing member 230a and the second inducing member 230b in response to the switching "on" of the first switch 244 or the second switch 248, that is, a close operation, and stops the supply of current to respective one of the first inducing member 230a and the second inducing member 230b in response to the switching "off" of the first switch 244 or the second switch 248, that is, an open operation. The first inducing member 230a and the second inducing member 230b generate heat in accordance with the supply of current.

In the present embodiment, a first end 232a of the first inducing member 230a is connected to the shape-memory member 220 by a third joint 255. The third joint 255 is arranged at a position close to a second end 228 of the shape-memory member 220 in the longitudinal direction. Also, a first end 232b of the second inducing member 230b is connected to the shape-memory member 220 by a third joint 272. The third joint 272 is arranged in the middle between a first end 226 and the second end 228 of the shape-memory member 220.

The following explains the configuration and arrangement of conductive wires 251, 253, 265, 261, and 263 electrically connecting the shape-memory member 220, the first inducing member 230a, the second inducing member 230b, and the power supply section 240 in the present embodiment. In also the present embodiment, the conductive wires 251, 253, 265, 261, and 263 that are three types of wires with lower electrical resistance per unit length than the inducing member 130 are used to improve the responsiveness of the shape-memory member 220 and the inducing members 230a and 230b to the power supplied from the power supply section 240.

Similar to the first conductive wires 51 and 61 of the first embodiment, the first conductive wires 251 and 261 each are a conductive wire with low electrical resistance per unit length that uses a material with lower electrical resistance than the first inducing member 230a and the second inducing member 230b. One end of the first conductive wire 251 is connected to a second end 234a of the first inducing member 230a by a first joint 252. The second end 234a is an end that is closer to the power supply section 240 than the first end 232a in the longitudinal direction of the variable stiffness section 250. One end of the first conductive wire 261 is connected to a second end 234b of the second inducing member 230b by a first joint 262. The second end 234b is an end that is closer to the power supply section 240 than the first end 232b. Note that the first end 232b is at a position closer to the power supply section 240 than the second end 234a.

Similar to the second conductive wires 53 and 63 of the first embodiment, the second conductive wires 253 and 263 each are a conductive wire that is thicker than the first conductive wires 251 and 261 and has low electrical resistance per unit length. One end of the second conductive wire 253 is connected to the other end of the first conductive wire 251 by a second joint 254. One end of the second conductive wire 263 is connected to the other end of the first conductive wire 261 by a second joint 264. The other end of the second conductive wire 253 is connected to the power supply section 240 (first power supply 242 and first switch 244). The other end of the second conductive wire 263 is connected to the power supply section (second power supply 246 and second switch 248). The power supply section 240 is controlled by a controller, which is not illustrated.

Similar to the third conductive wire 165 of the second embodiment, the third conductive wire 265 is desirably thicker than the second conductive wires 253 and 263, so as to have a low electrical resistance per unit length; however, it may have an electrical resistance that is similar to the second conductive wires 253 and 263 and lower than the first conductive wires 251 and 261. One end of the third conductive wire 265 is connected to a first end 226 of the shape-memory member 220 by a fourth joint 266. The other end of the third conductive wire 265 is connected to the power supply section 240.

The first joint 252 is an electrical contact between the first conductive wire 251 and the first inducing member 230a, and the first joint 262 is an electrical contact between the first conductive wire 261 and the second inducing member 230b. The second joint 254 is an electrical contact between the first conductive wire 251 and the second conductive wire 253, and the second joint 264 is an electrical contact between the first conductive wire 261 and the second conductive wire 263. The third joint 255 is an electrical contact between the shape-memory member 220 and the first inducing member 230a, and the third joint 272 is an electrical contact between the shape-memory member 220 and the second inducing member 230b. The fourth joint 266 is an electrical contact between the third conductive wire 265 and the shape-memory member 220. The connections by the joints 252, 262, 254, 255, 272, and 266 are, for example, also each formed by soldering, brazing, welding, or conductive adhesive. In the present embodiment, the joints 252, 262, 254, 264, 255, and 266 are displaced from one another so that their positions do not overlap in the longitudinal direction.

Similar to the second embodiment, in also the present embodiment, decreasing, as greatly as possible, the electrical resistance of the third conductive wire 265 that is assumed to have a certain length can prevent the voltage drop in the third conductive wire 265. Through the above configuration, the power can be efficiently supplied to the shape-memory member 220 and the inducing members 230a and 230b, so that the responsiveness of the shape-memory member 220 and that of the inducing members 230a and 230b to the supplied power can be improved.

In the present embodiment, the second conductive wires 253 and 263 differ from the third conductive wire 265 mainly in the respect that when the inducing members 220a and 220b are arranged in the variable stiffness section 250, and the power supply section 240 supplies currents to all of the inducing members, the current that flows through the third conductive wire 265 is a sum of the currents that flow through all the inducing members. That is, while the second conductive wire 253 (and the first conductive wire 251) transmits a current only to the first inducing member 230a, and the second conductive wire 263 (and the first conductive wire 261) transmits a current only to the second inducing member 230b, the third conductive wire 265 transmits currents to both the first inducing member 230a and the second inducing member 230b.

Therefore, according to the present embodiment, the inducing members 230a and 230b allows the bending stiffness of a flexible member, to which they are attached, to be controlled according to the positions of the inducing members 230a and 230b in the longitudinal direction of the variable stiffness section 250.

Note that when the inducing members are simultaneously energized, since the combined currents for all of the inducing members flow through the third conductive wire 265, it is desirable that its electrical resistance is lower than that of the second conductive wires 253 and 263. However, if the electrical resistance of the second conductive wires 253 and 263 is sufficiently low, the electrical resistance of the second conductive wires 253 and 263 and that of the third conductive wire 265 may be similar.

In also the present embodiment, since the shape-memory member 220 constituted by the conductive material and the third conductive wire 265 are connected by the fourth joint 266, the shape-memory member 220 is used as a conductive wire through which the current from the power supply section 240 flows. Through the above, wire-saving is possible even when the inducing members 230a and 230b exist.

Therefore, similar to the first and second embodiments, the present embodiment also provides the variable stiffness actuator 200 with improved responsiveness.

The variable stiffness section 250 has been explained as including two inducing members 230a and 230b; however, the number of the inducing members is not limited, so that the variable stiffness section 250 may include three or more inducing members. Individually changing the currents flowing through the respective inducing members by the power supply section 240 allows the bending stiffness of a flexible member, to which they are attached, to be controlled according to the positions of the inducing members.

Fourth Embodiment

Figure 5:
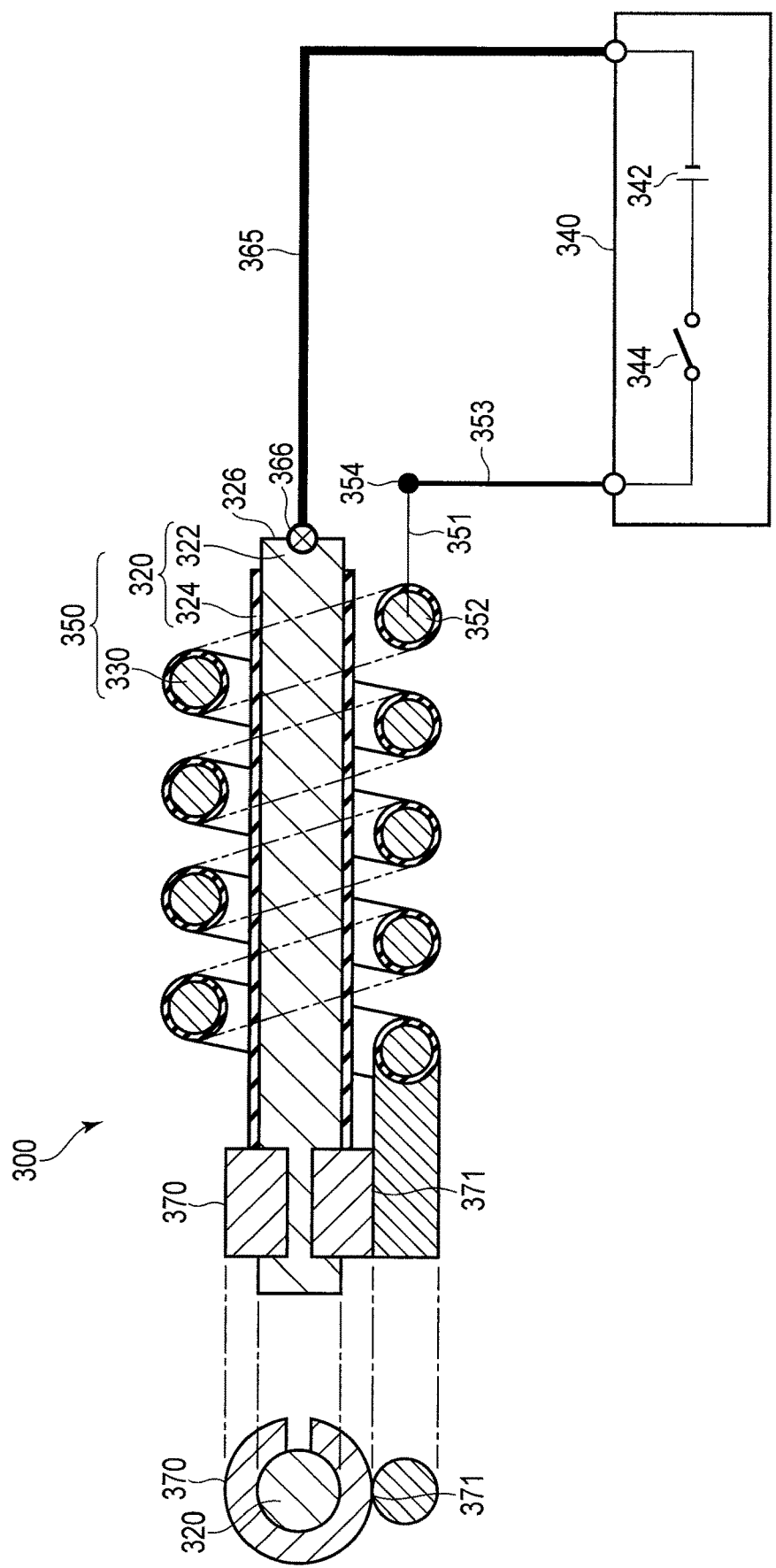
FIG. 5 is a figure showing a variable stiffness actuator according to a fourth embodiment.

FIG. 5 is a figure showing a variable stiffness actuator 300 according to a fourth embodiment of the present invention. The variable stiffness actuator 300 includes a shape-memory member 320, an inducing member 330, and a power supply section 340. The configurations and the arrangements of the shape-memory member 320 (main body 322 and insulating film 324), inducing member 330, and power supply section 340 (power supply 342 and switch 344) may all conform to those of the shape-memory member 120 (main body 122 and insulating film 124), inducing member 130, and power supply section 140 (power supply 142 and switch 144) of the second embodiment. The configurations and arrangements of conductive wires 351, 353, and 365, and joints 352, 354, and 366 may all conform to those of the conductive wires 151, 153, and 165, and the joints 152, 154, and 166 of the second embodiment. Therefore, the following explains the matters of such configurations and arrangements that are different from the second embodiment, and explanation of the common matters will be omitted.

In the present embodiment, the shape-memory member 320 and the inducing member 330 are connected by a fifth joint 371 through a connection member 370 at a first end 326. The connection member 370 is comprised of, for example, a cylindrical elastic member. The inner diameter of the connection member 370 is smaller than the outer diameter of the shape-memory member 320, so that the connection member 370 grips the shape-memory member 320 by its elastic contraction force. Further, the inducing member 330 and the connection member 370 are fixed by soldering etc. That is, through combining the gripping by elasticity and soldering, the shape-memory member 320 and the inducing member 330 can be connected by the fifth joint 371 through the connection member 370. The connection member 370 has conductivity and electrically connects the shape-memory member 320 to the inducing member 330. Further, although not shown in the figure, it is desirable that all of the joints 352, 354, and 366 are each protected by an insulating film.

In the present embodiment, it is desirable that all of the joints 352, 354, 366 and 371 form a good electrical connection achieved by, for example, soldering, brazing, welding, etc.; however, establishing a connection by conductive means such as conductive adhesive or conductive tape is also acceptable. Further, a connection through a connection member is also acceptable in consideration of durability and assembly. For example, pressure bonding (caulking), gripping by elasticity, pressing by screw etc. may be considered. As a matter of course, a combination of two or more of the above may be concurrently used.

Similar to the first to third embodiments, the present embodiment also provides the variable stiffness actuator 300 with improved responsiveness.

As explained above, according to each embodiment of the present invention, two or more types of conductive wires with lower electrical resistance per unit length than the inducing member (heating wire) are used in order to electrically connect the power supply section to the shape-memory member or the inducing member, which allows improving the responsiveness of the shape-memory member or the inducing member to the power (current) supplied by the power supply section.

By way of example, the description has assumed the flexible tube insertion apparatus to be the endoscope 70 and the flexible member to be the insertion section 72 of the endoscope 70; however, the flexible tube insertion apparatus is not limited to an endoscope, and it would be readily apparent to a person with ordinary skill in the art that the scope of the present invention widely covers any insertion device having an insertion section constituting a flexible member.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable stiffness actuator comprising:
    a shape-memory member;
    a heater configured to receive power to heat the shape-memory member so as to cause the shape-memory member to change from a first phase as a low stiffness state to a second phase as a high stiffness state showing a higher stiffness than the low stiffness state;
    a first conductive wire having a first end connected to the heater, the first conductive wire comprising a part of a power supply line for the heater; and
    a second conductive wire having a first end connected to a second end of the first conductive wire, the second conductive wire being thicker than the first conductive wire, and the second conductive wire having an electrical resistance per unit length lower than that of the first conductive wire.

2. The variable stiffness actuator according to claim 1, wherein a second end of the second conductive wire is connected to a power supply configured to supply the power to the heater for the heater to cause the change of phase.

3. The variable stiffness actuator according to claim 2, wherein a connection between the second end of the first conductive wire and the first end of the second conductive wire is arranged at a position closer to the power supply than a terminal end of the shape-memory member in a longitudinal direction.

4. The variable stiffness actuator according to claim 3, further comprising:
    a third conductive wire having a first end connected to an end of the shape-memory member,
    wherein the shape-memory member comprises a conductive material, and
    one end of the heater is connected to a part of the shape-memory member.

5. The variable stiffness actuator according to claim 4, wherein the third conductive wire has an electrical resistance per unit length that is lower than that of the first conductive wire and that is similar to or less than that of the second conductive wire.

6. The variable stiffness actuator according to claim 2, further comprising:
    a third conductive wire having a first end connected to an end of the shape-memory member,
    wherein the shape-memory member comprises a conductive material, and
    one end of the heater is connected to a part of the shape-memory member.

7. The variable stiffness controller according to claim 6, wherein the third conductive wire has an electrical resistance per unit length that is lower than that of the first conductive wire and that is similar to or less than that of the second conductive wire.

8. The variable stiffness actuator according to claim 6, wherein the heater comprising a plurality of heaters, and
    power supplied to each of the heaters is individually controlled by the power supply.

9. The variable stiffness actuator according to claim 1, wherein:
    the first conductive wire comprising a plurality of first conductive wires, each having first and second ends,
    the second conductive wire comprising a plurality of second conductive wires, each having first and second ends, and
    connections between the second ends of the plurality of first conductive wires and the first ends of the plurality of second conductive wires are arranged so as not to overlap with each other in a longitudinal direction of the shape-memory member.

10. An endoscope comprising:
    an insertion section; and
    the variable stiffness actuator according to claim 1 provided in the insertion section to provide different degrees of stiffness to the insertion section.

11. An endoscope comprising:
    an insertion section;
    a shape-memory member disposed along a longitudinal direction of the insertion section;
    a heater disposed along the shape-memory member and configured to receive power to heat the shape-memory member so as to cause the shape-memory member to change from a first phase as a low stiffness state to a second phase as a high stiffness state showing a higher stiffness than the low stiffness state;

a first conductive wire disposed in the insertion section, the first conductive wire having a first end connected to the heater, the first conductive wire comprising a part of a power supply line for the heater; and a second conductive wire having a first end connected to the second end of the first conductive wire, the second conductive wire being thicker than the first conductive wire and the second conductive wire having an electrical resistance per unit length lower than that of the first conductive wire.

* * * * *